United States Patent [19]

Förster et al.

[11] 4,271,186

[45] Jun. 2, 1981

[54] STILBENE COMPOUNDS AND INSECTICIDAL/ACARICIDAL COMPOSITIONS

[75] Inventors: Heinz Förster; Rainer Fuchs, both of Wuppertal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 53,562

[22] Filed: Jun. 29, 1979

[30] Foreign Application Priority Data

Jul. 21, 1978 [DE] Fed. Rep. of Germany ....... 2832213

[51] Int. Cl.³ ............... A01N 37/34; A01N 53/00; C07C 69/743; C07C 121/66
[52] U.S. Cl. ............... 424/304; 260/465 D; 424/282; 424/305; 424/308; 542/459; 560/8; 560/9; 560/55; 560/57; 560/101; 560/102; 560/105; 560/118; 560/124
[58] Field of Search ............ 260/340.5 R, 465 D; 560/8, 105, 118, 124, 9, 55, 101, 102; 424/304, 305, 306, 308; 542/459

[56] References Cited

U.S. PATENT DOCUMENTS

| | | | |
|---|---|---|---|
| 3,666,789 | 5/1972 | Itaya et al. | 560/124 |
| 3,835,176 | 9/1974 | Matsuo et al. | 560/124 X |
| 4,016,179 | 5/1977 | Fujimoto et al. | 260/465 D X |
| 4,130,657 | 12/1978 | Plummer | 560/124 X |

Primary Examiner—Dolph H. Torrence
Attorney, Agent, or Firm—Sprung, Felfe, Horn, Lynch & Kramer

[57] ABSTRACT

The invention relates to certain new stilbene derivatives of the general formula

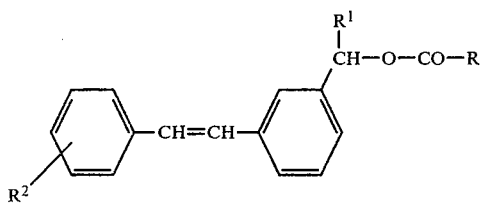

in which R, $R^1$ and $R^2$ have the below mentioned meaning, to a process for their preparation and to their use as arthropodicides, especially as insecticides and acaricides.

13 Claims, No Drawings

STILBENE COMPOUNDS AND INSECTICIDAL/ACARICIDAL COMPOSITIONS

The invention relates to certain new stilbene compounds, to insecticidal and acaricidal compositions containing them and to the use of such compounds as arthropodicides, especially as insecticides and acaricides. In additional aspect, the invention relates to a process for the preparation of such new stilbene compounds and to certain intermediates for use in the said process.

It is known that 2,2-dichlorovinyloxy-benzyl esters of certain cyclopropanecarboxylic acids, for example 2-(2,2-dichlorovinyl)-3,3-dimethyl-cyclopropane-1-carboxylic acid α-cyano-3'-(2,2-dichlorovinyloxy)-benzyl ester, can be used for combating insects, from DE-OS (German Published Specification) No. 2,554,883.

However, the action of these compounds is now always satisfactory, especially when low amounts are used.

The present invention now provides:

1. the stilbene derivatives of the general formula

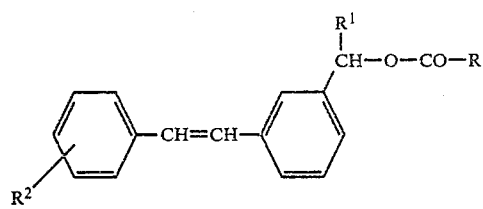

in which

R is an open-chain or cyclic alkyl radical which is optionally substituted by halogen, alkyl, cycloalkyl, alkenyl (which is optionally substituted by halogen), styryl (which is optionally substituted by halogen), phenyl (which is optionally substituted by halogen, alkyl, alkoxy, alkylthio, halogenoalkyl, halogenoalkoxy, halogenoalkylthio or methylenedioxy) or cycloalkenyl which is linked in a spirocyclic manner and is optionally benzofused, $R^1$ is hydrogen, cyano or alkynyl and
$R^2$ is hydrogen, halogen or alkyl;

2. a process for the preparation of a stilbene derivative of the formula (I), which is characterised in that a carboxylic acid of the general formula

R—COOH     (II)

in which

R has the meaning stated above, or a reactive derivative thereof, is reacted with an alcohol of the general formula

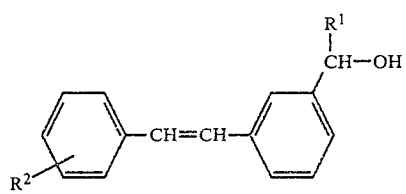

in which the radicals $R^1$ and $R^2$ have the meaning stated above, or a reactive derivative thereof, if appropriate in the presence of a diluent;

3. the alcohols of the general formula

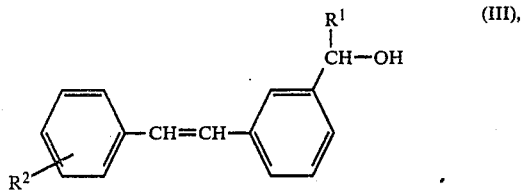

in which $R^1$ and $R^2$ have the meanings stated above;

4. a process for the preparation of an alcohol of the formula (III) according to 3 (above) wherein $R^1$ represents hydrogen, characterised in that a compound of the general formula

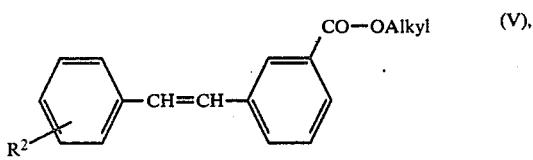

in which $R^2$ has the meaning indicated above and
"alkyl" represents $C_{1-4}$-alkyl, is reacted with a reducing agent, if appropriate in the presence of a diluent;

5. the compounds of the general formula

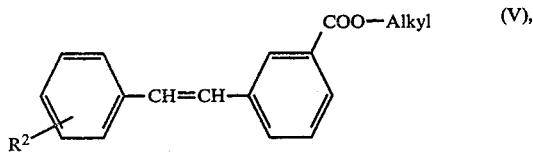

in which $R^2$ and "alkyl" have the meaning stated under 4 (above);

6. a process for the preparation of a compound of the formula (V) according to 5 (above), characterised in that (a) a phenylacetic acid derivative of the general formula

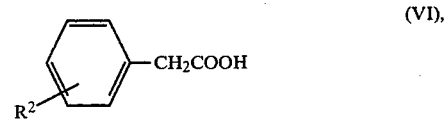

in which $R^2$ has the meaning stated above, is reacted with a 3-formylbenzoic acid ester of the general formula

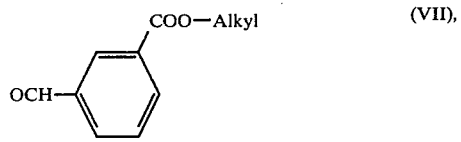

in which

"alkyl" has the meaning stated above, and the compound thereby obtained, of the general formula

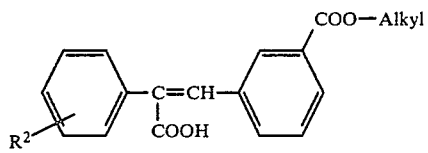 (VIII), in which

R² and "alkyl" have the meanings stated above, is decarboxylated, or (b) a benzylphosphonic acid ester of the general formula

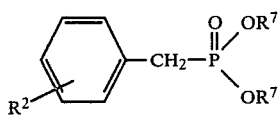 (IX), in which

R² has the meaning stated above and

R⁷ represents alkyl or phenyl, or the two radicals R⁷ together represent alkanediyl, is reacted with a base and with a 3-formylbenzoic acid ester of the formula (VII) according to 6a (above), or (c) a benzyltriphenylphosphonium salt of the general formula

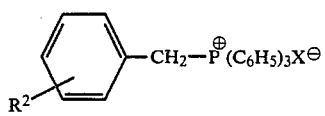 (IXa), in which

R² has the meaning stated above and

X represents halogen, is reacted with a base and with a 3-formylbenzoic acid ester of the formula (VII) according to 6a (above);

7. the formyl-stilbene derivatives of the general formula

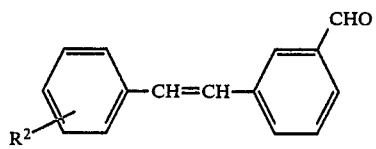 (IV), in which

R² has the meaning stated above; and 8. a process for the preparation of a formyl-stilbene derivative of the formula (IV) according to 7 (above), characterised in that an alcohol of the formula (III) according to 3 (above) is reacted with phosphorus tribromide and the bromomethyl-stilbene derivative formed, of the general formula

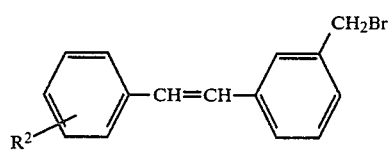 (X), in which

R² has the meaning stated above, is hydrolysed.

Preferred new stilbene derivatives of the formula (I) are those in which

R represents the radical

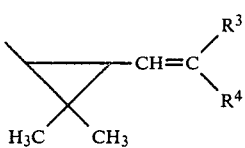

wherein

R³ represents hydrogen, methyl, chlorine or bromine and

R⁴ represents methyl, chlorine, bromine or optionally halogen-substituted phenyl, or wherein R³ and R⁴ together represent $C_2$-$C_6$-alkanediyl, or R represents the radical

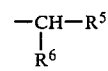

wherein

R⁵ represents phenyl which is optionally substituted by halogen, $C_1$-$C_4$-alkyl, $C_1$-$C_4$-alkoxy, $C_1$-$C_4$-alkylthio, $C_1$-$C_2$-halogenoalkyl, $C_1$-$C_2$-halogenoalkoxy, $C_1$-$C_2$-halogenoalkylthio or methylenedioxy and R⁶ represents isopropyl or cyclopropyl, or R represents one of the radicals

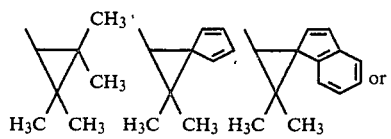

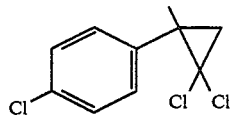

and in which

R¹ represents hydrogen, cyano or ethynyl and

R² represents hydrogen, halogen or $C_1$-$C_4$-alkyl

Particularly preferred stilbene derivatives of the formula (I) are those in which R represents the radical

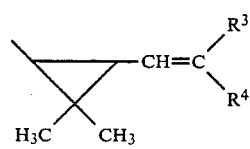

wherein

R³ represents hydrogen, methyl, chlorine or bromine and

R⁴ represents methyl, chlorine, bromine, phenyl or chlorophenyl, or wherein

R³ and R⁴ together represent alkanediyl with 2 to 5 carbon atoms, or

R represents the radical $$-\underset{\underset{R^6}{|}}{CH}-R^5$$

wherein

R[5] represents phenyl, chlorophenyl, methylphenyl, methoxyphenyl, methylthiophenyl, trifluoromethylphenyl, trifluoromethoxyphenyl, trifluoromethylthiophenyl or 3,4-methylenedioxyphenyl and R[6] represents isopropyl or cyclopropyl, or R represents one of the radicals

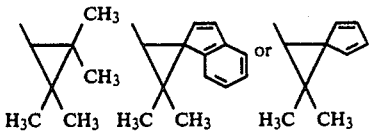

and in which

R[1] represents hydrogen or cyano and

R[2] represents hydrogen.

The various isomers and mixtures thereof are included in the general formula (I).

The stilbene derivatives of the formula (I) are each preferably obtained by a process in which a carboxylic acid chloride of the general formula R—CO—Cl          (XI), in which R has the meaning stated above, is reacted, as a reactive derivative of the corresponding carboxylic acid of the formula (II), with an alcohol of the general formula

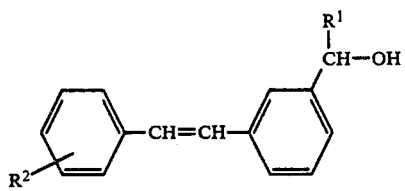

in which

R[1] and R[2] have the meanings stated above, if appropriate in the presence of an acid acceptor and if appropriate in the presence of a diluent. A particularly preferred process for the preparation of a compound of the formula (I) wherein R[1] represents cyano is characterised in that a carboxylic acid chloride of the formula (XI) above is reacted with a formyl-stilbene derivative of the general formula

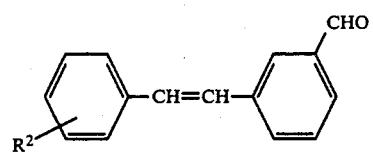

in which

R[2] has the meaning stated above, in the presence of at least an equimolar amount of an alkali metal cyanide, if appropriate in the presence of a catalyst and if appropriate in the presence of a diluent.

Surprisingly, the new stilbene derivatives of the formula (I) exhibit a better insecticidal action than the corresponding known products of analogous structure and the same type of action. They thus represent a valuable enrichment of the art.

If, for example, 3-(2-(4-chloro-phenyl)-vinyl)-benzyl alcohol and α-isopropyl-4-chloro-phenyl-acetic acid chloride, or 3-(2-phenyl-vinyl)-benzaldehyde and 2,2-dimethyl-3-(2-chloro-2-phenyl-vinyl)-cyclopropane-1-carboxylic acid chloride and also sodium cyanide are used as starting materials for the preparation of the stilbene derivatives of the formula (I), the corresponding reactions can be outlined by the equations which follow:

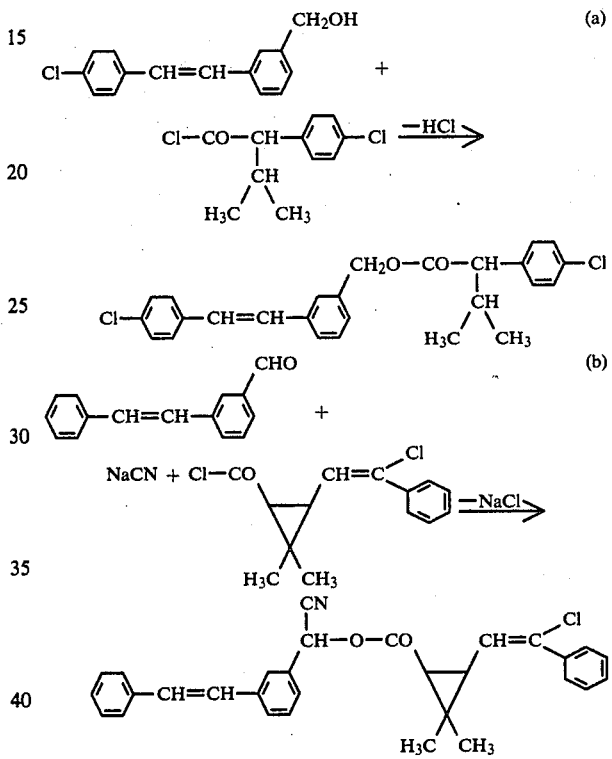

The formulae (II), (III), (IV) and (XI) provide definitions of the starting materials to be used.

In these formulae, the R, R[1] and R[2] preferably represent those radicals which have already been mentioned as preferred in the case of the definition of R, R[1] and R[2] in formula (I).

The carboxylic acids of the formula (II), or their reactive derivatives, such as acid chlorides or esters, to be used as starting compounds are known (see DE-OS (German Published Specification) Nos. 1,926,433, 2,231,312, 2,365,555, 2,605,828, 2,738,150 and 2,544,150).

Specific examples which may be mentioned of the carboxylic acid chlorides of the formula (XI) are: 2,2-dimethyl-3-(2-methyl-propen-1-yl)-, 2,2-dimethyl-3-(2,2-dichloro-vinyl)-, 2,2-dimethyl-3-(2,2-dibromo-vinyl)-, 2,2-dimethyl-3-(2-phenyl-vinyl)-, 2,2-dimethyl-3-(2-(4-chlorophenyl)-vinyl)-, 2,2-dimethyl-3-(2-chloro-2-phenyl-vinyl) and 2,2-dimethyl-3-(2-chloro-2-(4-chloro-phenyl)-vinyl-cyclopropane-1-carboxylic acid chloride, and also α-isopropyl-phenylacetic acid chloride, α-isopropyl-4-chlorophenyl-acetic acid chloride, α-isopropyl-4-trifluoromethylphenyl-acetic acid chloride, α-isopropyl-4-methoxy-phenylacetic acid chloride, α-isopropyl-4-trifluoromethoxy-phenylacetic acid chloride, α-isopropyl-4-methylthio-phenyl-acetic acid chloride, α-isopropyl-4-trifluoromethylthio-phenylacetic acid chloride, α-isopropyl-3,4-methylenedioxyphenylacetic acid chloride, α-cyclopropyl-phenylacetic acid chloride and α-cyclopropyl-4-chloro-phenyl-acetic acid chloride, and furthermore 3-cyclopropylidene-methyl-, 3-cyclobutylidene-methyl- and 3-cyclopentylidene-methyl-2,2-dimethyl-cyclopropane-1-carboxylic acid chloride, as well as 2,2,3,3-tetramethyl-cyclopropane-1-carboxylic acid chloride, 2,2-dimethyl-spiro(2,4)hepta-4,6-diene-1-carboxylic acid chloride and 3,3-dimethyl-spiro-(cyclopropane-1,1'-indene-(2-carboxylic acid chloride. Examples which may be mentioned of the carboxylic acids of the formula (II) are those from which the above-mentioned acid chlorides of the formula (XI) are derived.

The alcohols of the formula (III) to be used as starting compounds have not been described in the literature. Compounds of the formula (III) wherein $R^2$ has the meaning stated above and $R^1$ represents hydrogen, are obtained by a process in which alkoxycarbonyl-stilbene derivatives of the general formula $$R^2-\text{C}_6H_4-CH=CH-C_6H_4-CO-OAlkyl \quad (V),$$

wherein $R^2$ has the meaning indicated above, are reacted with a reducing agent, for example lithium aluminum hydride, if appropriate in the presence of an inert diluent, for example diethyl ether, tetrahydrofuran or dioxan, at a temperature between 0° and 50° C.

Working up can be effected in the customary manner, by a procedure in which, for example, the mixture is diluted with water, acidified with a strong acid, for example hydrochloric acid, and extracted with an organic solvent, for example toluene, and, after drying, the solvent is distilled off.

Examples which may be mentioned of the alcohols of the formula (III) are phenylvinyl-benzyl alcohols or styrylbenzyl alcohols, in particular 3-(2-phenylvinyl)-benzyl alcohol.

The formula (V) provides a definition of the alkoxycarbonyl-stilbene derivatives to be used as intermediate products. Preferably, in this formula, $R^2$ represents hydrogen and "alkyl" represents methyl or ethyl.

Examples which may be mentioned are: 3-(2-phenylvinyl)-benzoic acid methyl ester and ethyl ester.

The alkoxycarbonyl-stilbene derivatives of the formula (V) have not been described in the literature. They are obtained by a process in which (a) phenylacetic acid derivatives of the general formula $$R^2-C_6H_4-CH_2CO-OH \quad (VI),$$

wherein $R^2$ has the meaning stated above, are reacted with 3-formyl-benzoic acid esters of the general formula $$OHC-C_6H_4-CO-OAlkyl \quad (VII),$$

if appropriate in the presence of a basic catalyst, for example triethylamine, and if appropriate in the presence of a diluent, for example acetic anhydride, at temperatures between 20° and 200° C., preferably between 50° and 150° C., to give compounds of the general formula $$R^2-C_6H_4-C(CO-OH)=CH-C_6H_4-CO-OAlkyl \quad (VIII),$$

wherein $R^2$ has the meaning stated above, and the compounds of the formula (VIII) are decarboxylated, if appropriate after purification by recrystallisation, by heating to temperatures between 150° and 300° C., preferably between 200° and 250° C., if appropriate using a diluent, for example quinoline, and if appropriate using a catalyst, for example copper powder.

The working up in this procedure can be effected in the customary manner, for example by adding toluene and hydrochloric acid, separating off, washing and drying the organic phase, stripping off the solvent and distilling the residue in vacuo.

Alkoxycarbonyl-stilbene derivatives of the formula (V) are also obtained by a process in which (b) benzylphosphonic acid esters of the general formula $$R^2-C_6H_4-CH_2-P(=O)(OR^7)(OR^7) \quad (IX),$$

wherein $R^2$ has the meaning stated above and $R^7$ represents alkyl or phenyl, or the two radicals $R^7$ together represent alkanediyl, are reacted with a base, for example sodium methylate, if appropriate using a diluent, for example methanol and/or tetrahydrofuran, and the products are then reacted with 3-formyl-benzoic acid esters of the above formula (VII), at temperatures between −50° and +100° C., preferably at from −10° to +50° C.

Working up can then be effected in the customary manner, for example by taking up the reaction mixture in toluene, washing the mixture with water, drying the organic phase, stripping off the solvent and distilling the residue in vacuo and, if appropriate, recrystallising the product.

Alkoxycarbonyl-stilbene derivatives of the formula (V) are also obtained by a process in which (c) benzyl-triphenyl-phosphonium salts of the general formula

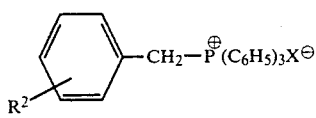

wherein
R² has the meaning stated above and
X represents halogen,
are reacted with a base, for example sodium ethylate, if appropriate using a diluent, for example ethanol, and the products are then reacted with a 3-formyl-benzoic acid ester of the formula (VII) above, preferably with 3-formyl-benzoic acid butyl ester, at temperatures between −50° and +100° C., preferably at from −10° to +50° C. Working up can be carried out in the customary manner, for example by concentrating the mixture, extracting the residue with toluene and stripping off the solvent in vacuo.

In general, the alkoxycarbonyl-stilbene derivatives obtained by preparative process (a) are present in the cis-configuration to the extent of over 90%; on the other hand, by process (b), the corresponding products are obtained in the trans-configuration to the extent of over 90%, and the isomers are obtained by process (c) in the ratio of about 1:1.

The formula (VI) provides a definition of the phenyl-acetic acid derivatives to be used as starting materials. Preferably, in this formula
R² represents hydrogen.
Phenylacetic acid may be mentioned as an example.
The phenylacetic acid derivatives of the formula (VI) are known compounds.

Formula (VII) provides a definition of the 3-formyl-benzoic acid esters also to be used as starting materials. Preferably, in this formula,
"alkyl" represents methyl or ethyl.
Examples which may be mentioned are: 3-formyl-benzoic acid methyl ester and 3-formyl-benzoic acid ethyl ester.
The 3-formyl-benzoic acid esters of the formula (VII) are known compounds (see Ber. Deut. Ges. Chem. 71 (1938), 335–341).

Formula (IX) provides a definition of the benzylphosphonic acid esters also to be used as starting materials. Preferably, in this formula,
R² represents hydrogen and
R⁷ represents methyl, ethyl or phenyl or the two R⁷ radicals together represent 2,2-dimethylpropane-1,3-diyl.
Examples which may be mentioned are benzyl-phosphonic acid dimethyl ester, diethyl ester and diphenyl ester.
The benzylphosphonic acid esters of the formula (IX) are known compounds.

Formula (IXa) provides a definition of the benzyltri-phenylphosphonium salts which can be used as starting materials. Preferably, in this formula,
R² represents hydrogen and
X represents chlorine.
Benzyl-triphenyl-phosphonium chloride may be mentioned as an example.
The benzyl-triphenyl-phosphonium salts of the formula (IXa) are known.

Formula (IV) provides a general definition of the formyl-stilbene derivatives (phenyl-vinyl-benzaldehyde derivatives) to be used as starting materials in the particularly preferred procedure for the preparation of compounds of the formula (I) wherein R¹ represents cyano. Preferably, in formula (IV),
R² represents hydrogen.
3-(2-Phenyl-vinyl)-benzaldehyde may be mentioned as an example of the compounds of the formula (IV).

The formyl-stilbene derivatives of the formula (IV) have not been described in the literature. They can be prepared by known processes starting from hydroxymethylstilbene derivatives of the general formula (III) wherein
R² has the meaning stated above and
R¹ represents hydrogen,
for example by a procedure in which hydroxymethyl-stilbene derivatives of the formula (III) are reacted with phosphorus tribromide, if appropriate using diluent, at temperatures between 0° and 50° C., the bromomethyl-stilbene derivatives formed, of the formula

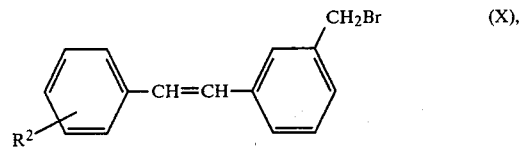

wherein
R² has the meaning stated above, are isolated in the customary manner, after washing the rection mixture with water and drying it and stripping off the solvent, and are reacted with hexamethylenetetramine, if appropriate using a diluent, at temperatures between 0° and 80° C., the crystalline adducts are heated to temperatures between 80° and 120° C. with aqueous acetic acid and, after cooling, the reaction products are extracted from the solution, to which hydrochloric acid has been added, with methylene chloride and are dried and distilled.

In general, the process for the preparation of the compounds of the formula (I) according to the invention is carried out using a diluent. Possible diluents are virtually any of the inert organic solvents, and if appropriate—when the process is carried out in a two-phase medium—also water, as the second solvent component. As organic solvents for the process according to the invention there may be mentioned: aliphatic and aromatic, optionally chlorinated hydrocarbons, for example pentane, hexane, heptane, benzene, toluene, xylene, methylene chloride, chloroform, carbon tetrachloride, chlorobenzene and dichlorobenzene; ethers, for example diethyl ether, tetrahydrofuran and dioxan; and nitriles, for example acetonitrile and propionitrile.

Any of the customary acid-binding agents can be used as the acid acceptors in the process, mentioned as preferred, using acid chlorides of the formula (XI) and alcohols of the formula (III) as starting materials. There may be mentioned in particular: alkali metal carbonates, for example sodium carbonate and potassium carbonate; alkali metal alcoholates, for example sodium methylate, potassium methylate, sodium ethylate and potassium ethylate; and aliphatic, aromatic or heterocyclic amines, for example trimethylamine, triethylamine, dimethylaniline, dimethylbenzylamine and pyridine.

In general, compounds used as catalysts in the processes, mentioned as particularly preferred, using formylstilbene derivatives of the formula (IV) and acid chlorides of the formula (XI) as starting materials are those which are usually used as auxiliaries for the phase transfer of reactants in the case of reactions in multiphase media. Tetraalkyl-ammonium salts and trialkylaralkyl-ammonium salts, for example tetrabutylammonium bromide and trimethyl-benzyl-ammonium chloride, may be mentioned in particular. Examples of alkali metal cyanides which can be used are sodium cyanide and potassium cyanide.

The reaction temperature can be varied within a relatively wide range. In general, the reaction is carried out between 0° and 100° C., preferably between 10° and 50° C.

In general, the reactions are carried out under normal pressure.

For carrying out the reactions, the starting components are in general employed in equimolar amounts. An excess of one or other of the components brings no substantial advantages. In general, the reactants are brought together in one or more of the stated diluents and the mixture is stirred for several hours in order to bring the reaction to completion. The reaction mixture is then shaken with toluene/water and the organic phase is separated off, washed with water and dried. After distilling off the solvent in vacuo, the new compounds are in general obtained in the form of oils, some of which cannot be distilled without decomposition. However, they can be freed from the last volatile constituents by so-called "incipient distillation", that is to say by prolonged heating to moderately elevated temperatures under reduced pressure, and purified in this manner. The refractive index is used for their characterisation.

The active compounds are well tolerated by plants, have a favourable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porecillio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Grylloralpa spp., *Locusta migratoria migratoriodes, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Ericsoma lanigerum, Hyalopterus arundinis, Macrosiphum avenae,* Myzus spp.; *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Chroristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemilineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cehopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects and acarids) which comprises applying to the arthropods, or to a habitat thereof, a compound of the present invention alone or in the form of a composition containing as active ingredients a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The insecticidal and acaricidal activity of the compounds of this invention is illustrated by the following biotest Examples.

In these Examples, the compounds according to the present invention are each identified by the number (given in brackets) of the corresponding preparative Example, which will be found later in this specification.

EXAMPLE A

Laphygma test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined. 100% meant that all of the caterpillars had been killed whereas 0% indicated that none of the caterpillars had been killed.

In this test, for example, the following compounds showed a superior activity compared to the prior art: (1), (6) and (7).

EXAMPLE B

Test with parasitic adult cattle ticks (*Boophilus microplus* res.).

Solvent: alkylaryl polyglycol ether

To produce a suitable preparation of active compound, the mixture substance in question was mixed with the stated solvent in the ratio of 1:2 and the concentrate thus obtained was diluted with water to the desired concentration.

10 adult cattle ticks (*B. microplus* res.) were dipped for 1 minute into the active compound preparation to be tested. After transfer into plastic beakers and storage in a climatically controlled chamber, the degree of destruction was determined.

In this test, for example, the following compounds showed a superior action compared to the prior art: (1) and (2).

EXAMPLE C

Test with parasitic fly larvae

Emulsifier: 80 parts by weight of alkylaryl polyglycol ether

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, for example, the following compounds showed a superior action compared to the prior art: (1) and (2).

PREPARATIVE EXAMPLES

Example 1

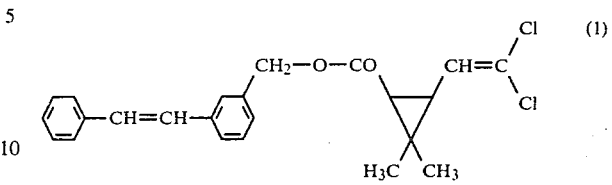

5 g (0.0238 mol) of 3-(2-phenylvinyl)-benzyl alcohol (about 90% cis-isomer) and 5.4 g (0.0238 mol) of 2,2-dimethyl-3-dichlorovinyl-cyclopropanecarboxylic acid chloride were dissolved in 100 ml of anhydrous toluene, and 3 g of pyridine, dissolved in 50 ml of anhydrous toluene, were added dropwise at 20°-25° C., whilst stirring. The mixture was then stirred at 25° C. for a further 3 hours. The reaction mixture was poured into 150 ml of water, to which 10 ml of concentrated hydrochloric acid had been added, and the organic phase was separated off and washed again with 100 ml of water. The toluene phase was then dried over sodium sulphate and the solvent was distilled off under a waterpump vacuum. Last residues of solvent were removed by subjecting the product to brief incipient distillation at a bath temperature of 60° C./1 mm Hg. 5.6 g (58.7% of theory) of 2,2-dimethyl-3-dichlorovinyl-cyclopropanecarboxylic acid 3'-(2-phenylvinyl)-benzyl ester were obtained as a yellow oil with the refractive index $n_D^{24}$: 1.5853 (isomer mixture with a cis-stilbene proportion of about 90%.

Example 2

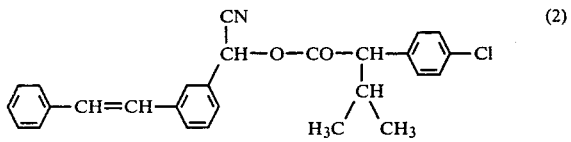

4.16 g (0.02 mol) of 3-(2-phenyl-vinyl)-benzaldehyde and 4.62 g (0.02 mol) of α-isoproyl-4-chlorophenylacetic acid chloride were added dropwise, together, to a mixture of 1.5 g of sodium cyanide, 2 ml of water, 40 ml of n-hexane and 0.5 g of tetrabutylammonium bromide at 20°-25° C., whilst stirring, and the mixture was then stirred at 20°-25° C. for 4 hours. 300 ml of toluene were then added to the reaction mixture, and the mixture was extracted by shaking twice with 300 ml of water each time. The organic phase was separated off and dried over magnesium sulphate and the solvent was distilled off under a waterpump vacuum. Last residues of solvent were removed by subjecting the product to brief incipient distillation at a bath temperature of 60° C./1 mm Hg. 6 g (69.9% of theory) of α-isopropyl-4-chlorophenylacetic acid 3-(2-phenylvinyl)-α-cyanobenzyl ester were obtained as a yellow oil with the refractive index $n_D^{22}$: 1.5879 (isomer mixture with a cis-stilbene proportion of about 90%).

The following compounds were prepared analogously to Example 1 or 2 (cis-stilbene proportion in each case about 90%):

| Example No. | Formula | Yield (% of theory) | Refractive index: |
|---|---|---|---|
| 3 | (phenyl)–CH=CH–(phenyl)–CH$_2$–O–CO–CH(–C$_6$H$_4$–Cl)–CH(CH$_3$)(CH$_3$) | 65.9 | $n_D^{22}$:1.5911 |
| 4 | (phenyl)–CH=CH–(phenyl)–CH$_2$–O–CO–[cyclopropane(H$_3$C)(CH$_3$)]–CH=C(Cl)(C$_6$H$_4$Cl) | 76.9 | $n_D^{22}$:1.6049 |
| 5 | (phenyl)–CH=CH–(phenyl)–CH$_2$–O–CO–[cyclopropane(H$_3$C)(CH$_3$)]–CH=CBr$_2$ | 81.6 | $n_D^{22}$:1.5849 |
| 6 | (phenyl)–CH=CH–(phenyl)–CH(CN)–O–CO–[cyclopropane(H$_3$C)(CH$_3$)]–CH=CCl$_2$ | 70.4 | $n_D^{22}$:1.5846 |
| 7 | (phenyl)–CH=CH–(phenyl)–CH(CN)–O–CO–[cyclopropane(H$_3$C)(CH$_3$)]–CH=CBr$_2$ | 77.7 | $n_D^{22}$:1.5907 |
| 8 | (phenyl)–CH=CH–(phenyl)–CH(CN)–O–CO–[cyclopropane(H$_3$C)(CH$_3$)]–CH=C(Cl)(C$_6$H$_4$Cl) | 49.8 | |
| 9 | (phenyl)–CH=CH–(phenyl)–CH$_2$–O–CO–CH(–C$_6$H$_4$–OCF$_3$)–CH(CH$_3$)(CH$_3$) | 55.0 | $n_D^{23}$:1.5424 |
| 10 | (phenyl)–CH=CH–(phenyl)–CH(CN)–O–CO–CH(–C$_6$H$_4$–OCF$_3$)–CH(CH$_3$)(CH$_3$) | | |
| 11 | (phenyl)–CH=CH–(phenyl)–CH(CN)–O–CO–CH(–benzodioxole)–CH(CH$_3$)(CH$_3$) | | |
| 12 | (phenyl)–CH=CH–(phenyl)–CH$_2$–O–CO–[cyclopropane(H$_3$C)(CH$_3$)]–CH=CH–C$_6$H$_4$–Cl | | |
| 13 | (phenyl)–CH=CH–(phenyl)–CH(CN)–O–CO–[cyclopropane(H$_3$C)(CH$_3$)]–CH=CH–C$_6$H$_4$–Cl | 57.8 | |

-continued
| Example No. | Formula | Yield (% of theory) | Refractive index: |
|---|---|---|---|
| 14 | 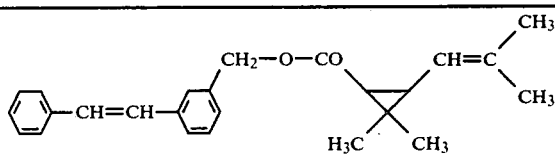 | 64.8 | $n_D^{22}$:1.5812 |
| 15 | 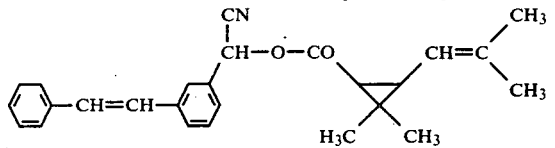 | | |
| 16 | 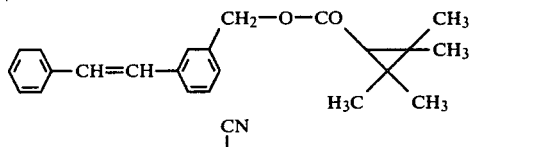 | | |
| 17 | 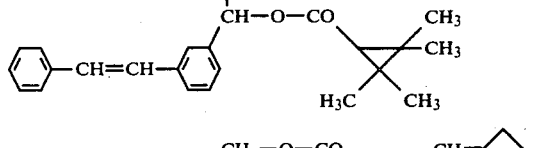 | | |
| 18 | 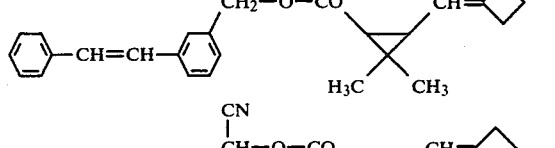 | 80.6 | $n_D^{23}$:1,5811 |
| 19 | 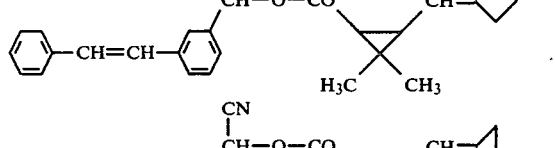 | 62.9 | |
| 20 | 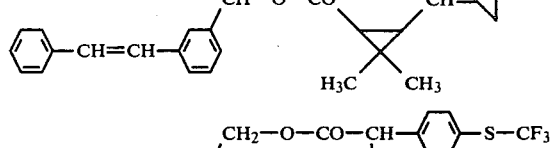 | | |
| 21 | 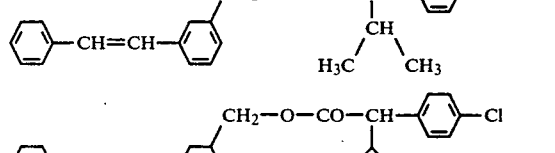 | 61.2 | $n_D^{23}$:1.5662 |
| 22 | 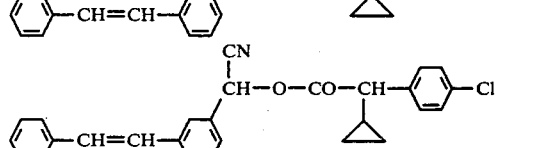 | | |
| 23 | 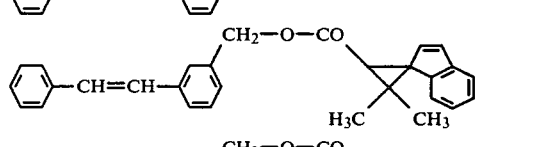 | 58.5 | |
| 24 | 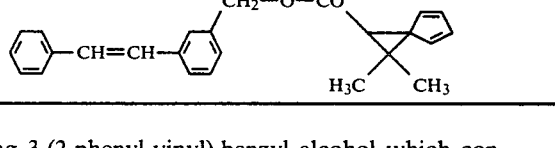 | | |
| 25 | 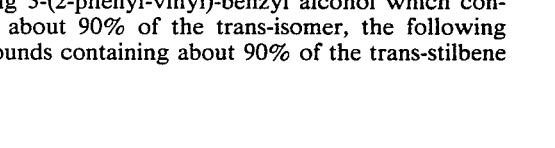 | | |
Using 3-(2-phenyl-vinyl)-benzyl alcohol which contained about 90% of the trans-isomer, the following compounds containing about 90% of the trans-stilbene

| Example No. | Formula | Yield (% of theory) | Refractive index: |
|---|---|---|---|
| 26 | 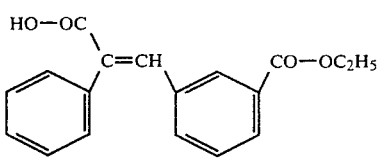 | 83.1 | $n_D^{22}$:1.6058 |
| 27 |  | 82.4 | $n_D^{22}$:1.6119 |
| 28 |  |  |  |
| 29 | 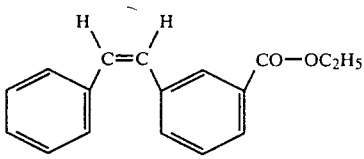 | 58.7 |  |

Preparation of the starting compounds:
(a) cis-stilbene derivatives

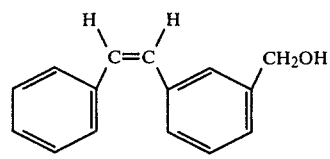

17.8 g (0.01 mol) of 3-formyl-benzoic acid ethyl ester, 13.6 g (0.1 mol) of phenylacetic acid and 10 g of triethylamine were dissolved in 30 ml of acetic anhydride and the solution was heated to the reflux for 5 hours. After cooling, 300 ml of water were added to the reaction mixture and the mixture was then heated to the boil for 20 minutes. The solid residue was then decanted off hot, and this was recrystallised from methanol, to which a little water had been added. 13 g (43.9% of theory) of 3-(2-carboxy-2-phenylvinyl)-benzoic acid ethyl ester were obtained as light yellow crystals of melting point 139°–140° C. (isomer mixture with a cis proportion of about 90%).

1 g of copper powder was added to 13 g (0.044 mol) of 3-(2-carboxy-2-phenyl-vinyl)-benzoic acid ethyl ester, dissolved in 100 ml of quinoline, and the mixture was heated to 220° C., whilst stirring, until no further evolution of carbon dioxide could be observed (about 1 hour). The mixture was then cooled immediately to room temperature. After adding 300 ml of toluene to the reaction mixture, it was extracted by shaking twice with 100 ml of concentrated hydrochloric acid each time and then washed with 500 ml of water. The organic phase was separated off and dried over magnesium sulphate, the solvent was distilled off under a waterpump vacuum and the residue was distilled in vacuo. 10 g (90.2% of theory) of 3-(2-phenyl-vinyl)-benzoic acid ethyl ester were obtained as a yellow oil with the boiling point 165°–170° C./2 mm Hg (isomer mixture with a cis proportion of about 90%).

10 g (0.03 mol) of 3-(2-phenyl-vinyl)-benzoic acid ethyl ester, dissolved in 50 ml of dry tetrahydrofuran, were added dropwise to 2.5 g of lithium aluminium hydride in 50 ml of anhydrous tetrahydrofuran at 25°–30° C., whilst stirring thoroughly. The reaction mixture was then subsequently stirred at 22° C. for 10 hours and then cooled to 0° C. and ice-water was added dropwise, whilst stirring, until no further evolution of hydrogen could be observed (60 ml). The precipitate which had formed was dissolved by adding 30 ml of concentrated hydrochloric acid dropwise, and the reaction mixture was then extracted twice with 100 ml of toluene each time. The organic phase was separated off and dried over sodium sulphate and the solvent was distilled off under a waterpump vacuum. Last residues of solvent were removed by subjecting the product to brief incipient distillation at a bath temperature of 60° C./1 mm Hg. 5 g (61% of theory) of 3-(2-phenyl-vinyl)-benzyl alcohol were obtained as a yellow oil with the refractive index $n_D^{22}$: 1.6286 (isomer mixture with a cis proportion of about 90%).

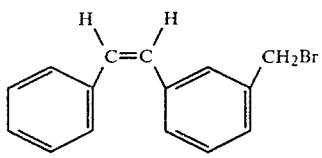

21 g (0.1 mol) of 3-(2-phenyl-vinyl)-benzyl alcohol were dissolved in 200 ml of anhydrous toluene, and 10 g of phosphorus tribromide were added dropwise at 0°–10° C., whilst stirring. The mixture was then stirred at 10° C. for 2 hours and at room temperature for a further 2 hours. The reaction mixture was then extracted by shaking twice with 500 ml of water each time, the organic phase was separated off and dried over magnesium sulphate and the solvent was distilled off under a waterpump vacuum. Last residues of solvent were removed by subjecting the product to brief incipient distillation at a bath temperature of 60° C./2 mm Hg. 23 g (84.2% of theory) of 3-(2-phenyl-vinyl)-benzyl bromide were obtained as a yellow oil with the refractive index $n_D^{22}$: 1.6376 (isomer mixture with a cis proportion of about 90%).

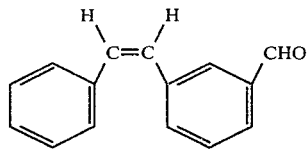

47 g (0.172 mol) of 3-(2-phenyl-vinyl)-benzyl bromide and 60 g of hexamethylenetetramine in 400 ml of methylene chloride were heated under reflux for 3 hours, the mixture was then cooled to 5°–10° C. and the precipitate which had formed was filtered off. This was washed with 100 ml of methylene chloride and sucked dry, and then heated under reflux in 600 ml of 50% strength aqueous acetic acid for 3 hours. Thereafter, the mixture was cooled to room temperature and 45 ml of concentrated hydrochloric acid were added. 800 ml of water were then added to the reaction mixture, the mixture was extracted twice with 200 ml of methylene chloride each time and the organic phase was then separated off and dried over sodium sulphate. The solvent was distilled off under a waterpump vacuum and the oily residue was then distilled. 15 g (41.9% of theory) of 3-(2-phenyl-vinyl)-benzaldehyde were obtained as a colourless liquid with the boiling point 145°–150° C./2 mm Hg (isomer mixture with a cis proportion of about 90%).

(b) trans-stilbene derivatives

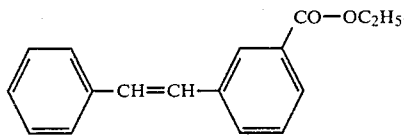

45.6 g (0.2 mol) of benzylphosphonic acid diethyl ester, dissolved in 50 ml of tetrahydrofuran, were added dropwise to a mixture of 300 ml of tetrahydrofuran and 46.4 g (0.22 mol) of a methanolic sodium methylate solution at 0°–5° C., whilst stirring. The mixture was subsequently stirred at 0° C. for 2 hours and 35.6 g (0.2 mol) of 3-formyl-benzoic acid ethyl ester, dissolved in 50 ml of tetrahydrofuran, were then added dropwise, also at 0° C. and whilst stirring. The reaction mixture was then stirred at 20°–25° C. for 12 hours, 300 ml of toluene were subsequently added and the mixture was then extracted by shaking twice with 600 ml of water each time. The organic phase was separated off and dried over magnesium sulphate and the solvent was distilled off under a waterpump vacuum. The oily residue was distilled at 160°–190° C. and under a pressure of 3 mm Hg. The semi-crystalline product thus obtained was dissolved in a little petroleum ether and the solution was cooled to 0° C. The crystals which had precipitated were filtered off and dried. 19 g (37.7% of theory) of 3-(2-phenyl-vinyl)-benzoic acid ethyl ester were obtained as colourless crystals with the melting point 82° C. (isomer mixture, about 90% transconfiguration).

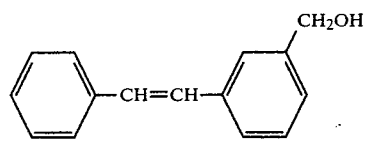

3-(2-Phenyl-vinyl)-benzoic acid ethyl ester (with a trans proportion of 90%) could be reduced to 3-(2-phenyl-vinyl)-benzyl alcohol (isomer mixture, about 90% transconfiguration) with lithium aluminium hydride by the process described above (see "cis-stilbene derivatives").

Yield: 13.5 g (85.7% of theory), melting point 84° C., colourless crystals.

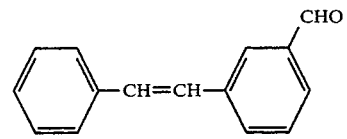

Starting from 3-(2-phenyl-vinyl)-benzyl alcohol (trans proportion about 90%), 3-(2-phenyl-vinyl)-benzaldehyde was obtained, analogously to the preparation route described above, in a yield of 82.4% of theory and as colourless crystals with the melting point 90° C. (isomer mixture with a trans proportion of about 90%).

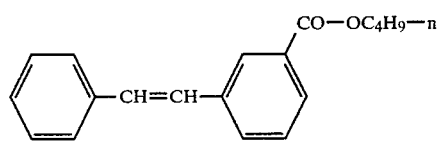

2.3 g (0.1 mol) of sodium were dissolved in 50 ml of ethanol and this solution was added dropwise to a solution of 38.9 g (0.1 mol) of benzyl-triphenyl-phosphonium chloride in 150 ml of ethanol at an internal temperature of −5° to 0° C. 20.6 g (0.1 mol) of 3-formyl-benzoic acid n-butyl ester were then added to this mixture and the mixture was kept at 0° to 5° C. for two hours, whilst stirring, and allowed to come slowly to room temperature. After concentrating the mixture, the residue was extracted with toluene, the toluene extract was filtered and the solvent was distilled off from the filtrate in vacuo. 21.3 g (75% theory) of 3-(2-phenyl-vinyl)-benzoic acid n-butyl ester were obtained as a slightly yellowish oil (cis/trans isomer mixture in the ratio 1:1).

It will be understood that the specification and examples are illustrative but not limitative of the present invention and that other embodiments within the spirit and scope of the invention will suggest themselves to those skilled in the art.

What is claimed:

1. Stilbene compound of the formula

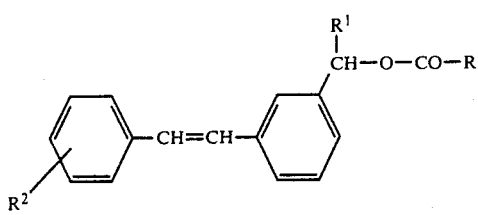

wherein
R is the radical

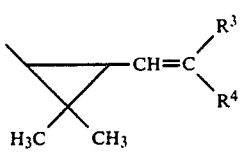

wherein
R¹ is hydrogen, cyano or ethynyl;
R² is hydrogen, halogen or alkyl;
R³ is hydrogen, methyl, chlorine or bromine; and
R⁴ is methyl, chlorine, bromine or optionally halogen-substituted phenyl,
or wherein
R³ and R⁴ together are C₂-C₆-alkanediyl.

2. Stilbene compound of the formula

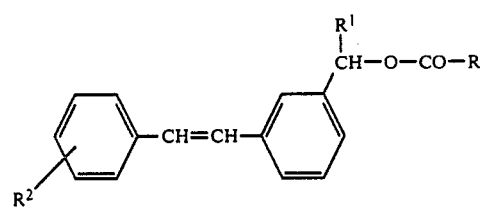

wherein
R is the radical

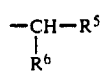

wherein
R¹ is hydrogen, cyano or ethynyl;
R² is hydrogen, halogen or alkyl;
R⁵ is phenyl which is optionally substituted by halogen, C₁-C₄-alkyl, C₁-C₄ alkoxy, C₁-C₄-alkylthio, C₁-C₂-halogenoalkyl, C₁-C₂-halogenoalkoxy, C₁-C₂-halogenoalkylthio or methylenedioxy or
R⁶ is isopropyl or cyclopropyl.

3. Stilbene compound of the formula

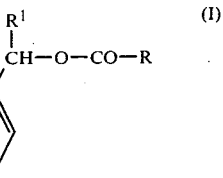

wherein
R is one of the radicals

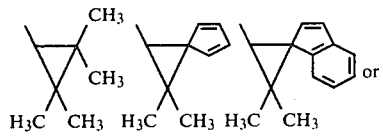

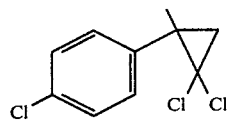

and in which
R¹ is hydrogen, cyano or ethynyl and
R² is hydrogen, halogen or C₁-C₂-alkyl.

4. Stilbene compound as claimed in claim 1 wherein
R is the radical

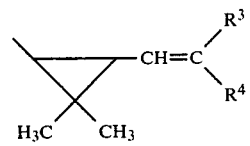

wherein
R³ is hydrogen, methyl, chlorine or bromine and
R⁴ is methyl, chlorine, bromine, phenyl or chlorophenyl,
or wherein
R³ and R⁴ together represent alkanediyl with 2 to 5 carbon atoms.

5. Stilbene compound as claimed in claim 1 designated 2,2-dimethyl-3-dichlorovinyl-cyclopropanecarboxylic acid 3'-(2-phenylvinyl)-benzyl ester.

6. Stilbene compound as claimed in claim 1 designated 2,2-dimethyl-3-dibromovinyl-cyclopropanecarboxylic acid 3'-(2-phenylvinyl)-benzyl ester.

7. Stilbene compound as claimed in claim 1 designated 2,2-dimethyl-3-dichlorovinyl-cyclopropanecarboxylic acid 3'-(2-phenylvinyl)-α-cyano-benzyl-ester.

8. Stilbene compound as claimed in claim 1 designated 2,2-dimethyl-3-dibromovinyl-cyclopropanecarboxyic acid 3'-(2-phenylvinyl)-α-cyanobenzyl ester.

9. Stilbene compound as claimed in claim 2 wherein

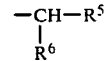

R⁵ is phenyl, chlorophenyl, methylphenyl, methoxyphenyl, methylthiophenyl, trifluoromethylphenyl, trifluoromethoxyphenyl, trifluoromethylthiophenyl or 3,4-methylenedioxyphenyl and
R⁶ is isopropyl or cyclopropyl.

10. Stilbene compound as claimed in claim 3 wherein

R is one of the radicals

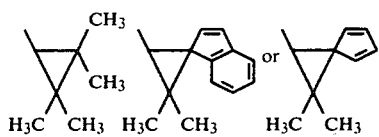

and in which

R[1] is hydrogen or cyano and

R[2] is hydrogen.

11. Stilbene compound designated alpha-isopropyl-4-trifluoromethoxy-phenyl-acetic acid 3-(2-phenylvinyl)-alpha-cyanobenzyl ester.

12. Silbene compound designated alpha-isopropyl-4-trifluoromethoxy-phenyl-acetic acid 3-(2-phenylvinyl)-benzyl ester.

13. A method of combating arthropods which comprises applying to the arthropods or their habitat a stilbene compound, in an effective amount, and wherein said compound is selected from 2,2-dimethyl-3-dichlorovinylcyclopropanecarboxylic acid 3'-(2-phenylvinyl)-benzyl ester 2,2-dimethyl-3-dibromovinyl-cyclopropanecarboxylic acid 3'-(2-phenylvinyl)-benzyl ester 2,2-dimethyl-3-dichlorovinyl-cyclopropanecarboxylic acid 3'-(2-phenylvinyl)-alpha-cyano-benzyl-ester 2,2-dimethyl-3-dibromovinyl-cyclopropanecarboxylic acid 3'-(2-phenylvinyl)alpha-cyanobenzyl ester, and alpha-isopropyl-4-tricfuoromethoxy-acetic acid 3-(2-phenylvinyl)-alpha-cyanobenzyl ester.

* * * * *